United States Patent
Sudo et al.

(10) Patent No.: US 10,076,230 B2
(45) Date of Patent: Sep. 18, 2018

(54) ENDOSCOPE SYSTEM AND OPERATION METHOD OF ENDOSCOPE SYSTEM

(71) Applicant: OLYMPUS CORPORATION, Tokyo (JP)

(72) Inventors: Masaru Sudo, Hachioji (JP); Hideyuki Kugimiya, Hachioji (JP); Ryo Koshida, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/625,562

(22) Filed: Jun. 16, 2017

(65) Prior Publication Data

US 2017/0303771 A1 Oct. 26, 2017

Related U.S. Application Data

(63) Continuation of application No. PCT/JP2016/076459, filed on Sep. 8, 2016.

(30) Foreign Application Priority Data

Feb. 25, 2016 (JP) .................. 2016-034688

(51) Int. Cl.
*A62B 1/04* (2006.01)
*A61B 1/04* (2006.01)
(Continued)

(52) U.S. Cl.
CPC ...... *A61B 1/00114* (2013.01); *A61B 1/00117* (2013.01); *A61B 1/05* (2013.01); *H04N 7/10* (2013.01); *H04N 7/22* (2013.01); *H04N 5/2256* (2013.01); *H04N 5/3575* (2013.01); *H04N 5/363* (2013.01); *H04N 5/37455* (2013.01); *H04N 2005/2255* (2013.01)

(58) Field of Classification Search
CPC ............ H04N 5/378; A61B 1/05; A61B 1/051
See application file for complete search history.

(56) References Cited

U.S. PATENT DOCUMENTS

6,458,078 B1 * 10/2002 Ludtke ............... A61B 1/00013
348/E5.029
2009/0248036 A1 * 10/2009 Hoffman ............... A61B 1/045
606/130
(Continued)

FOREIGN PATENT DOCUMENTS

JP 2002-343985 A 11/2002
JP 2002-354458 A 12/2002
(Continued)

*Primary Examiner* — Rebecca Volentine
(74) *Attorney, Agent, or Firm* — Scully, Scott, Murphy & Presser, P.C.

(57) ABSTRACT

An endoscope system includes: a CMOS image pickup device configured to output digital signals of a plurality of systems; E/O converters configured to convert the digital signals of the plurality of systems to optical signals respectively; optical fibers configured to transmit the optical signals of the plurality of systems respectively; a transmission amount changer configured to convert a data amount of the digital signal of at least one system; and a metal wire configured to transmit the digital signal, the data amount of which is converted by the transmission amount changer.

10 Claims, 4 Drawing Sheets

(51) Int. Cl.
*A61B 1/06* (2006.01)
*A61B 1/00* (2006.01)
*H04N 7/10* (2006.01)
*H04N 7/22* (2006.01)
*A61B 1/05* (2006.01)
*H04N 5/225* (2006.01)
*H04N 5/3745* (2011.01)
*H04N 5/357* (2011.01)
*H04N 5/363* (2011.01)

(56) References Cited

U.S. PATENT DOCUMENTS

2010/0261961 A1* 10/2010 Scott .................. A61B 1/00193
                                                                    600/111
2012/0310081 A1* 12/2012 Adler .................. A61B 5/0035
                                                                    600/427
2012/0320176 A1* 12/2012 Tanaka ............... A61B 1/00006
                                                                    348/65
2013/0012777 A1*  1/2013 Baum ................. A61B 1/00013
                                                                    600/110
2013/0096380 A1*  4/2013 Matsuzawa ........ A61B 1/00013
                                                                    600/109
2013/0208101 A1*  8/2013 Ono ................... A61B 1/00193
                                                                    348/65
2017/0014019 A1*  1/2017 Ogura ................ A61B 1/00126
2017/0202432 A1*  7/2017 Michihata .......... A61B 1/00006

FOREIGN PATENT DOCUMENTS

| JP | 2003-019127 A | 1/2003 |
| JP | 2007-053675 A | 3/2007 |
| JP | 2009-088852 A | 4/2009 |
| JP | 2009-095554 A | 5/2009 |
| JP | 2015-000173 A | 1/2015 |
| WO | WO 2016/002415 A1 | 1/2016 |

* cited by examiner

ENDOSCOPE SYSTEM AND OPERATION METHOD OF ENDOSCOPE SYSTEM

CROSS REFERENCE TO RELATED APPLICATION

This application is a continuation application of PCT/JP2016/076459 filed on Sep. 8, 2016 and claims benefit of Japanese Application No. 2016-034688 filed in Japan on Feb. 25, 2016, the entire contents of which are incorporated herein by this reference.

BACKGROUND OF THE INVENTION

1. Field of the Invention

The present invention relates to an endoscope system configured to transmit a digital signal from an image pickup apparatus by an optical transmitting member and a metal transmitting member, and an operation method of the endoscope system.

2. Description of the Related Art

An endoscope having a function as an image pickup apparatus includes an elongated insertion portion configured to acquire an optical image at a distal end portion. Then, by inserting the insertion portion into a subject, an inside of the subject that cannot be observed from an outside can be observed as an endoscopic image.

In particular, in an electronic endoscope, an optical image of a subject is photoelectrically converted using an image pickup device or the like, transmitted to a signal processor (processor) as an electric signal, processed in the signal processor, then displayed as an endoscopic image at a display portion such as a monitor, and observed.

In an endoscope system using such an electronic endoscope, an endoscopic image of higher definition is demanded in order to make a more certain judgement.

Since a data amount is large for an image pickup signal of the high-definition endoscopic image, an endoscope system that, instead of transmitting an electric signal using a metal conducting wire, converts an electric image pickup signal to an optical signal, transmits the optical signal using an optical fiber, converts the optical signal to the electric image pickup signal after transmission, and provides the signal for signal processing or the like has been proposed.

For example, Japanese Patent Application Laid-Open Publication No. 2015-173 describes an endoscope system in which an endoscope includes an insertion portion including a distal end portion where an image pickup signal processing portion configured to output a first video signal and a second video signal and an E/O conversion portion configured to convert the first video signal to an optical signal are disposed, an optical fiber configured to transmit the optical signal and a metal conducting wire configured to transmit the second video signal, and a processor includes a selector configured to output either one of the first video signal for which the optical signal is reconverted and the second video signal and a video signal processing portion configured to process the first video signal or the second video signal outputted from the selector to output a first image signal or a second image signal.

Here, since the optical fiber is made of glass, the optical fiber is weak against bending and twisting compared to a signal cable for an electric signal configured using the metal conducting wire, and may be snapped in a middle of observation. Therefore, in a technology described in the publication, in a case that abnormality (for example, a fault due to breakage, degradation or stain of an optical connector or the like) occurs in the optical fiber for example and an image cannot be appropriately displayed during an operation in a first mode of generating an image from the first video signal, the operation is shifted to a second mode, the second video signal, a bit rate of which is lower than the bit rate of the first video signal transmitted by the optical fiber, is transmitted by the metal conducting wire, and the image is generated using the second video signal.

SUMMARY OF THE INVENTION

An endoscope system according to an aspect of the present invention includes: an image pickup apparatus configured to pick up an image of a subject and output the image as digital signals of a plurality of systems; an electrooptic converter configured to convert the digital signals of the plurality of systems outputted from the image pickup apparatus to optical signals respectively and output the optical signals; a plurality of optical transmitting members provided so as to respectively transmit the optical signals of the plurality of systems outputted from the electrooptic converter; a metal transmitting member provided so as to transmit a digital signal of at least one system among the digital signals of the plurality of systems outputted from the image pickup apparatus; and a transmission amount changer configured to convert the digital signal of at least one system which is a target to be transmitted by the metal transmitting member to a digital signal of a data amount suitable for transmission by the metal transmitting member, and output the digital signal to the metal transmitting member.

In an operation method of an endoscope system according to another aspect of the present invention, an image pickup apparatus picks up an image of a subject and outputs the image as digital signals of a plurality of systems, an electrooptic converter converts the digital signals of the plurality of systems outputted from the image pickup apparatus to optical signals respectively and outputs the optical signals, optical transmitting members provided in plurality respectively transmit the optical signals of the plurality of systems outputted from the electrooptic converter, a metal transmitting member transmits a digital signal of at least one system among the digital signals of the plurality of systems outputted from the image pickup apparatus, and a transmission amount changer converts the digital signal of at least one system which is a target to be transmitted by the metal transmitting member to a digital signal of a data amount suitable for transmission by the metal transmitting member, and outputs the digital signal to the metal transmitting member.

DETAILED DESCRIPTION OF THE PREFERRED EMBODIMENT(S)

Hereinafter, an embodiment of the present invention will be described with reference to the drawings.

Embodiment 1

Figure 1:
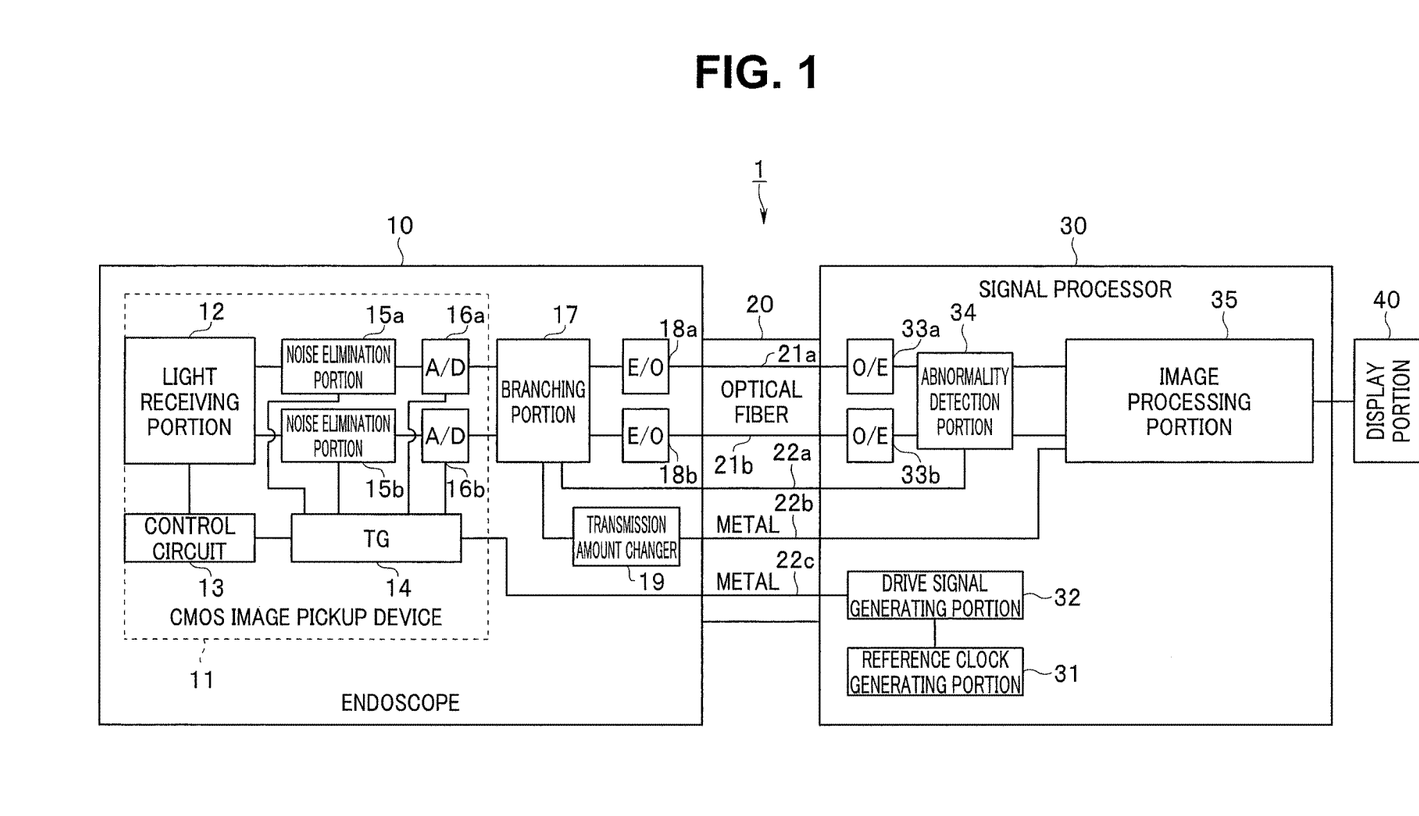
FIG. 1 is a diagram illustrating a configuration of an endoscope system in an embodiment 1 of the present invention.

FIG. 1 to FIG. 5 illustrate the embodiment 1 of the present invention, and FIG. 1 is a block diagram illustrating a configuration of an endoscope system 1.

The endoscope system 1 includes: an endoscope 10 configured to pick up an image of a subject and generate a signal; a connection cable 20 configured to transmit the signal generated by the endoscope 10; a signal processor 30 configured to process the signal transmitted through the connection cable 20; and a display portion 40 configured to display video based on a video signal generated by performing processing by the signal processor 30.

The endoscope 10 includes a CMOS image pickup device 11, a branching portion 17, electrooptic converters (E/O converters) 18a and 18b, and a transmission amount changer 19.

Here, the endoscope 10 may be either one of a rigid endoscope and a flexible endoscope.

For example, in a case that the endoscope 10 is configured as a rigid endoscope, the CMOS image pickup device 11 is disposed at a camera head, reflected light from the subject is received at a distal end of the rigid endoscope, object light is transmitted by an image guide fiber bundle, and photoelectric conversion is performed in the CMOS image pickup device 11 at the camera head. In addition, the branching portion 17, the E/O converters 18a and 18b, and the transmission amount changer 19 are also disposed at the camera head.

On the other hand, in the case that the endoscope 10 is configured as a flexible endoscope, the CMOS image pickup device 11 is disposed at a distal end portion of an elongated insertion portion. The branching portion 17, the E/O converters 18a and 18b and the transmission amount changer 19 can be also disposed at the insertion portion, however, from a viewpoint of narrowing a diameter of the insertion portion, it is preferable to dispose the branching portion 17, the E/O converters 18a and 18b and the transmission amount changer 19 inside an operation portion that operates the insertion portion.

The CMOS image pickup device 11 is an image pickup apparatus configured to pick up the image of the subject and output the image as digital signals of a plurality of systems, and includes a light receiving portion 12, a control circuit 13, a timing generator (TG) 14, noise elimination portions 15a and 15b, and A/D converters 16a and 16b.

The light receiving portion 12 includes a plurality of two-dimensionally arrayed pixels that perform the photoelectric conversion, photoelectrically converts an optical image of the subject formed by an image pickup optical system not shown in the figure, and outputs an analog image pickup signal (electric signal).

Figure 2:
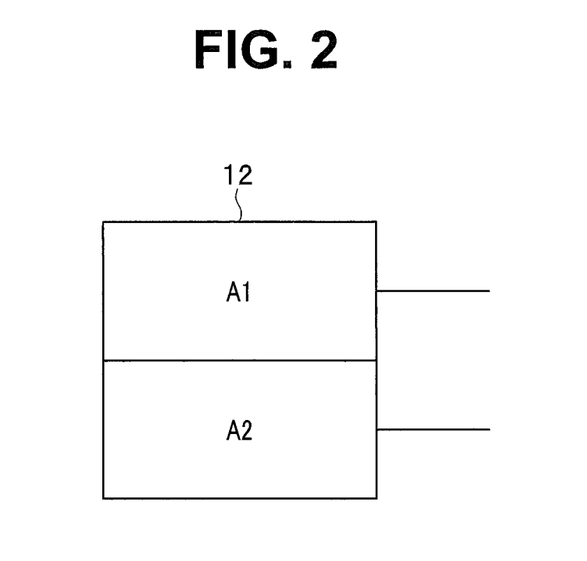
FIG. 2 is a diagram illustrating an example of a case that output from a light receiving portion is two systems, in the embodiment 1.
Figure 3:
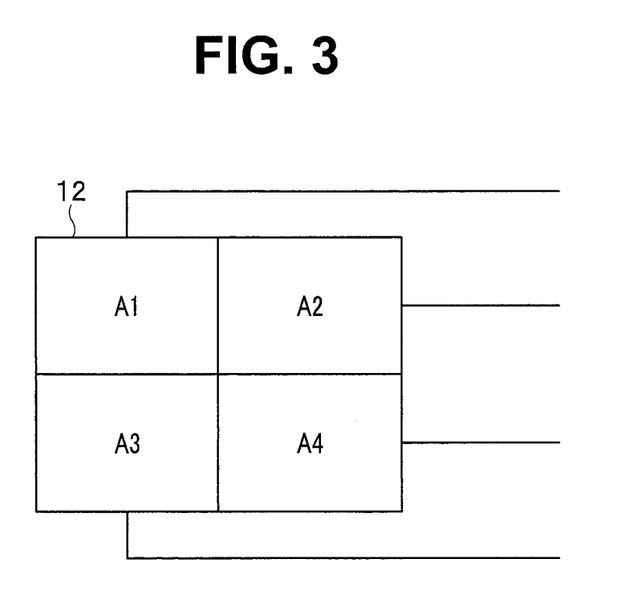
FIG. 3 is a diagram illustrating an example of a case that the output from the light receiving portion is four systems, in the embodiment 1.

Here, FIG. 2 is a diagram illustrating an example of a case that output from the light receiving portion 12 is two systems, and FIG. 3 is a diagram illustrating an example of a case that the output from the light receiving portion 12 is four systems.

The CMOS image pickup device 11 of the present embodiment is configured to pick up the image of the subject and output the image as the digital signals of the plurality of systems. Specifically, the light receiving portion 12 is divided into a plurality of image pickup areas, and an image pickup signal is outputted as a different system for each image pickup area.

In the example illustrated in FIG. 2, the light receiving portion 12 is divided into two of a first image pickup area A1 and a second image pickup area A2, and the image pickup signals from the respective image pickup areas A1 and A2 are outputted as the different systems.

In addition, in the example illustrated in FIG. 3, the light receiving portion 12 is divided into four of the first to fourth image pickup areas A1-A4, and the image pickup signals from the respective image pickup areas A1-A4 are outputted as the different systems.

Note that a division number of the image pickup areas may be an appropriate number equal to or larger than 2, and a division method of the image pickup areas is not limited to a method of division into respective local areas as illustrated in FIG. 2 and FIG. 3. For example, a division method of, when n is defined as a natural number, setting all (2n-1) lines which are odd-numbered lines as the first image pickup area and setting all 2n lines which are even-numbered lines as the second image pickup area may be adopted.

FIG. 1 illustrates a configuration example in the case of adopting the output of two systems as illustrated in FIG. 2, and the case that the output is two systems will be described as an example similarly hereinafter.

The control circuit 13 performs control of starting exposure by resetting each pixel arrayed in the light receiving portion and reading a reset signal, and ending the exposure by reading a pixel signal of each pixel at a point of time of reaching predetermined exposure time.

The timing generator (TG) 14 generates a timing signal based on a drive signal from a drive signal generating portion 32 to be described later of the signal processor 30, and supplies the timing signal to the respective circuits inside the CMOS image pickup device 11, for example, the control circuit 13, the noise elimination portions 15a and 15b, and the A/D converters 16a and 16b. Therefore, the respective circuits inside the CMOS image pickup device 11 perform an operation in conjunction based on the timing signal. Note that the timing signal generated by the timing generator (TG) 14 may be supplied also to other components inside the endoscope 10, the branching portion 17 and the transmission amount changer 19 for example, to link the operation.

The noise elimination portion 15a performs noise elimination processing on the image pickup signal from the image pickup area A1 in FIG. 2 for example, and the noise elimination portion 15b performs the noise elimination processing on the image pickup signal from the image pickup area A2 for example. Specifically, the noise elimination portions 15a and 15b eliminate reset noise by performing correlated double sampling of subtracting the reset signal from the pixel signal obtained by the exposure to each pixel signal. Note that it is needless to say that the noise elimination portions 15a and 15b may be configured to eliminate the other noise further.

The A/D converter 16a converts the analog image pickup signal outputted from the noise elimination portion 15a to a digital image pickup signal (electric signal), and the A/D converter 16b converts the analog image pickup signal outputted from the noise elimination portion 15b to the digital image pickup signal (electric signal).

The branching portion 17 is a branching device, and outputs either one of the digital image pickup signal outputted from the A/D converter 16a and the digital image pickup signal outputted from the A/D converter 16b to the transmission amount changer 19 as needed, based on a control signal from an abnormality detection portion 34 to be described later of the signal processor 30.

For example, the branching portion 17 performs switching so as to connect all the digital signals of the plurality of systems outputted from the CMOS image pickup device 11 only to the E/O converters 18a and 18b in the case that the abnormality is not detected by the abnormality detection portion 34, and connect all the digital signals of the system transmitted by an optical fiber 21b or 21a (optical transmitting member) in which the abnormality is not detected among the digital signals of the plurality of systems outputted from the CMOS image pickup device 11 only to the electrooptic converter and connect all the digital signals of the system transmitted by the optical fiber 21b or 21a (optical transmitting member) in which the abnormality is detected only to the transmission amount changer 19 (consequently, only to a metal wire 22b which is a metal transmitting member to be described later) in the case that the abnormality is detected by the abnormality detection portion 34.

Note that, here, attention is paid to a fact that a probability that abnormality (for example, a fault due to breakage, degradation or stain of an optical connector or the like) simultaneously occurs in the plurality of optical fibers (in the example of FIG. 1, the optical fiber 21a and the optical fiber 21b) is low, the branching portion 17 outputs either one of the image pickup signal from the image pickup area A1 and the image pickup signal from the image pickup area A2 to the transmission amount changer 19.

However, without being limited to the configuration, it may be possible to cope with the case that the abnormality simultaneously occurs in the plurality of optical fibers. For example, the plurality of metal wires 22b that are the metal transmitting member to be described later may be provided so as to cope with the plurality of systems to simultaneously transfer the image pickup signals from the plurality of image pickup areas.

Or, by increasing a decimation rate (or a compression rate) to be described later of the transmission amount changer 19, even when only one system of the metal wire 22b is provided, the image pickup signals from the plurality of image pickup areas can be transferred. In this case, depending on whether the abnormality of the optical fiber occurs only in one system or occurs simultaneously in the plurality of systems, the decimation rate (or the compression rate) of the transmission amount changer 19 is adaptively changed. Specifically, the decimation rate (or the compression rate) is defined as x when the abnormality occurs only in one system, the decimation rate (or the compression rate) is changed to x/n when the abnormality occurs in n systems or the like.

Figure 4:
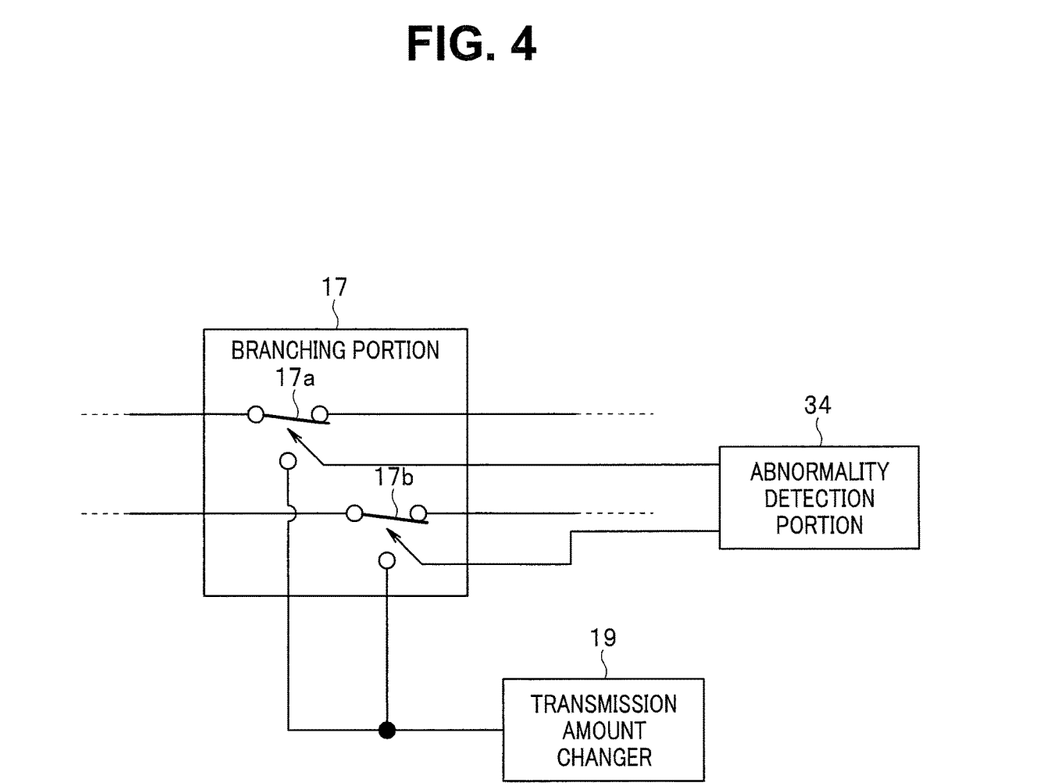
FIG. 4 is a diagram illustrating a schematic configuration example of a branching portion in the embodiment 1.

Here, FIG. 4 is a diagram illustrating a schematic configuration example of the branching portion 17.

In the configuration example illustrated in FIG. 4, the digital image pickup signal outputted from the A/D converter 16a is transmitted through a switch 17a to the E/O converter 18a, and the digital image pickup signal outputted from the A/D converter 16b is transmitted through a switch 17b to the E/O converter 18b.

Then, when the switch 17a is switched, the digital image pickup signal outputted from the A/D converter 16a is transmitted to the transmission amount changer 19 instead of the E/O converter 18a. When the switch 17b is switched, the digital image pickup signal outputted from the A/D converter 16b is transmitted to the transmission amount changer 19 instead of the E/O converter 18b.

Note that, in the configuration example illustrated in FIG. 4, the image pickup signal is outputted to only either one of an optical fiber 21a (or an optical fiber 21b) side and a metal wire 22b side, however, the image pickup signal may be outputted to both of the optical fiber 21a (or the optical fiber 21b) side and the metal wire 22b side (that is, the image pickup signals of all the systems may be outputted to the optical fiber and the image pickup signal of the system in which the abnormality has occurred may be outputted to the metal wire 22b) (or, in the case of providing the plurality of systems of the metal wires 22b, the image pickup signals of all the systems may be outputted also to the metal wires 22b, further).

In addition, in the configuration illustrated in FIG. 1, the branching portion 17 is provided outside the CMOS image pickup device 11, however, the branching portion 17 may be provided inside the CMOS image pickup device 11 as a circuit on a semiconductor substrate, similarly to the noise elimination portions 15a and 15b and the A/D converters 16a and 16b.

The E/O converters 18a and 18b are the electrooptic converters configured to convert the digital signals of the plurality of systems outputted from the CMOS image pickup device 11 to optical signals respectively and output the optical signals. That is, the E/O converters 18a and 18b include a light emitting element and a light emitting element drive portion for example, and by the light emitting element drive portion driving the light emitting element according to the inputted electric signals, generate and output the optical signals.

Here, the E/O converter 18a converts the digital image pickup signal outputted from the A/D converter 16a through the branching portion 17 to the optical signal, and the E/O converter 18b converts the digital image pickup signal outputted from the A/D converter 16b through the branching portion 17 to the optical signal.

The transmission amount changer 19 converts the digital signal of at least one system which is a target to be transmitted by the metal wire 22b that is the metal transmitting member to a digital signal of a data amount suitable for transmission by the metal wire 22b, and outputs the digital signal to the metal wire 22b.

Specifically, the transmission amount changer 19 converts only the digital signal of the system transmitted by the optical fibers 21a and 21b (optical transmitting members) in which the abnormality is detected by the abnormality detection portion 34 to be described later of the signal processor 30 to the digital signal of the data amount suitable for the transmission by the metal wire 22b which is the metal transmitting member, and outputs the digital signal to the metal wire 22b.

At the time, the transmission amount changer 19 performs change to the data amount that can be transmitted by the metal wire 22b, by performing data decimation processing (as a more specific example, pixel decimation processing) to the digital image pickup signal inputted from the branching portion 17.

However, the data amount is converted by the transmission amount changer 19 not only by the decimation processing, and other technologies may be used. As an example, when increase of processing loads can be allowed, a data compression technology (encoding or the like) may be used, or both of the decimation processing and data compression may be performed.

Next, the connection cable 20 is connected to the endoscope 10 at one end and connected to the signal processor 30 at the other end respectively, and is for transmitting signals between the endoscope 10 and the signal processor 30. The connection cable 20 includes the optical fibers 21a and 21b that transmit the optical signal and the metal wires 22a, 22b and 22c that transmit the electric signal.

The optical fibers 21a and 21b are arranged in parallel inside the connection cable 20, and are the plurality of optical transmitting members provided so as to transmit the optical signals of the plurality of systems outputted from the E/O converters 18a and 18b respectively.

Specifically, the optical fiber 21a transmits the optical signal from the E/O converter 18a relating to the image pickup area A1, and the optical fiber 21b transmits the optical signal from the E/O converter 18b relating to the image pickup area A2.

The metal wire 22a is the metal transmitting member, and transmits the control signal (electric signal) from the abnormality detection portion 34 to be described later of the signal processor 30 to the branching portion 17.

The metal wire 22b is the metal transmitting member provided so as to transmit the digital signal of at least one system among the digital signals of the plurality of systems outputted from the CMOS image pickup device 11. Specifically, the metal wire 22b transmits the digital image pickup signal (electric signal) outputted from the transmission amount changer 19 to an image processing portion 35 to be described later of the signal processor 30.

The metal wire 22c is the metal transmitting member, and transmits the drive signal (electric signal) from the drive signal generating portion 32 to be described later of the signal processor 30 to a TG 14.

Note that, since the plurality of optical fibers 21a and 21b arranged in the connection cable 20 are formed to be an extremely narrow diameter (for example, a diameter 0.125 mm) with quartz glass for example and is very weak, the respective optical fibers 21a and 21b are primarily coated with an ultraviolet curing resin for example, then covered with a protective tube for example further, and protected. At the time, the plurality of primarily coated optical fibers 21a and 21b may be gathered and covered with the protective tube, or each of the plurality of primarily coated optical fibers 21a and 21b may be individually coated with the protective tube.

In addition, the metal wires 22a, 22b and 22c arranged in the connection cable 20 may be also coated with the protective tube respectively for example, or may be protected altogether with the protective tube after two or more are turned to an insulation state.

Then, the plurality of optical fibers 21a and 21b and the metal wires 22a, 22b and 22c may be appropriately arranged inside the connection cable 20, however, it is preferable to be symmetrical to a cable center axis for example. When an arrangement symmetrical to the cable center axis is adopted, the connection cable 20 can be bent in an arbitrary direction by an identical curvature and does not become easy to bend in a specific direction and hard to bend in another specific direction so that the connection cable 20 can be easily handled.

As the arrangement symmetrical to the cable center axis, for example, the metal wires 22a, 22b and 22c are symmetrically arranged around the plurality of gathered optical fibers 21a and 21b at an axial center, or the plurality of optical fibers 21a and 21b are symmetrically arranged around the gathered metal wires 22a, 22b and 22c at the axial center. In the case of adopting any arrangement, the metal wires 22a, 22b and 22c achieve a function as tension members that protect the optical fibers 21a and 21b from tension applied to the connection cable 20.

Subsequently, the signal processor 30 includes a reference clock generating portion 31, the drive signal generating portion 32, optoelectric converters (O/E converters) 33a and 33b, the abnormality detection portion 34, and the image processing portion 35.

The reference clock generating portion 31 includes a crystal oscillator for example, and generates a reference clock of a frequency to be a reference.

The drive signal generating portion 32 generates the drive signal for driving the CMOS image pickup device 11, based on the reference clock generated by the reference clock generating portion 31. The drive signal generated by the drive signal generating portion 32 is transmitted through the metal wire 22c to the TG 14 as described above.

Note that, in the example illustrated in FIG. 1, the reference clock generating portion 31 and the drive signal generating portion 32 are disposed inside the signal processor 30, however, only the drive signal generating portion 32 or both of the reference clock generating portion 31 and the drive signal generating portion 32 may be configured to be disposed inside the endoscope 10. In the case of disposing only the drive signal generating portion 32 inside the endoscope 10, the metal wire 22c transmits the reference clock generated by the reference clock generating portion 31 to the drive signal generating portion 32. On the other hand, in the case of disposing both of the reference clock generating portion 31 and the drive signal generating portion 32 inside the endoscope 10, need of the metal wire 22c is eliminated.

The optoelectric converters (O/E converters) 33a and 33b convert the optical signals transmitted by the optical fibers 21a and 21b which are the plurality of optical transmitting members to the electric signals respectively and output the electric signals. For example, the O/E converters 33a and 33b include a photodiode configured to convert the optical signal to a current signal and a transimpedance amplifier configured to convert the current signal to a voltage signal, convert the inputted optical signals to the electric signals and output the electric signals.

Here, the O/E converter 33a converts the optical signal inputted through the optical fiber 21a to the digital image pickup signal, and O/E converter 33b converts the optical signal inputted through the optical fiber 21b to the digital image pickup signal.

Note that, in the example illustrated in FIG. 1, the O/E converters 33a and 33b are arranged inside the signal processor 30, however, the O/E converters 33a and 33b may be arranged at an end portion on the side of the signal processor 30 inside the connection cable 20, inside a connector to be connected to the signal processor 30 for example.

The abnormality detection portion 34 is an abnormality detector configured to detect the abnormality of the respective optical fibers 21a and 21b which are the plurality of optical transmitting members (consequently, the abnormality of respective signal systems transmitted through the optical fibers 21a and 21b), based on the electric signals outputted from the O/E converters 33a and 33b. Specifically, the abnormality detection portion 34 detects whether or not the abnormality has occurred in the optical fiber 21a based on the digital image pickup signal outputted from the O/E converter 33a, and detects whether or not the abnormality has occurred in the optical fiber 21b based on the digital image pickup signal outputted from the O/E converter 33b.

Then, in the case that the abnormality of the optical fiber 21b or 21a is detected, the abnormality detection portion 34 turns on an abnormality flag (see FIG. 5) to be described later (note that the abnormality flag is off in the case that the abnormality is not detected), transmits the control signal through the metal wire 22a to the branching portion 17, and controls the switch 17b or 17a connected to the optical fiber 21b or 21a in which the abnormality is detected to be switched to the side of the transmission amount changer 19. Thus, the image pickup signal of the system with the abnormality that has occurred in the optical fiber is transmitted through the metal wire 22b.

Note that the abnormality detection portion 34 detects the abnormality based on the electric signals outputted from the O/E converters 33a and 33b here, however, without being limited to the configuration, the abnormality detection portion 34 may be configured to detect the abnormality by directly detecting the optical signals transmitted through the optical fibers 21a and 21b, for example.

The image processing portion 35 is a video signal generator configured to generate a video signal based on the electric signals of the plurality of systems outputted from the O/E converters 33a and 33b in the case that the abnormality is not detected by the abnormality detection portion 34 (in the case of determining that the abnormality flag is off), and generate the video signal by combining the electric signal of the system with no abnormality detected, which is outputted from the O/E converter 33a or 33b, and the digital signal transmitted by the metal wire 22b in the case that the abnormality is detected by the abnormality detection portion 34 (in the case of determining that the abnormality flag is on).

Specifically, in the case that the abnormality of the optical fibers 21a and 21b is not detected by the abnormality detection portion 34, the image processing portion 35 configures the image of an entire screen by integrating the digital image pickup signal relating to the image pickup area A1 outputted from the O/E converter 33a and the digital image pickup signal relating to the image pickup area A2 outputted from the O/E converter 33b, performs general image processing such as demosaicking processing, white balance processing, noise reduction processing, color matrix processing or gamma conversion processing, and generates and outputs the video signal.

On the other hand, the image processing portion 35 includes an interpolation processing portion, and in the case that the abnormality of the optical fiber 21b or 21a is detected by the abnormality detection portion 34, interpolates the decimated image pickup signal of the image pickup area A2 or A1 inputted through the metal wire 22b so as to be matched with a pixel number of the image pickup signal transmitted as the optical signal. Then, the image processing portion 35 configures the image of the entire screen by integrating the interpolated image pickup signal and the image pickup signal transmitted through the normal optical fiber 21a or 21b and converted in the O/E converter 33a or 33b, performs the general image processing as described above, and generates and outputs the video signal.

Note that, in the case that the transmission amount changer 19 is configured to use the data compression technology (encoding or the like), the image processing portion 35 includes an image expansion portion configured to perform a data expansion technology (decoding or the like) (or, in the case that the transmission amount changer 19 is configured to perform both of the decimation processing and data compression, the image processing portion 35 includes both of the interpolation processing portion and the image expansion portion).

The display portion 40 is configured including a monitor or the like, and observably displays the video signal generated by the image processing portion 35.

Figure 5:
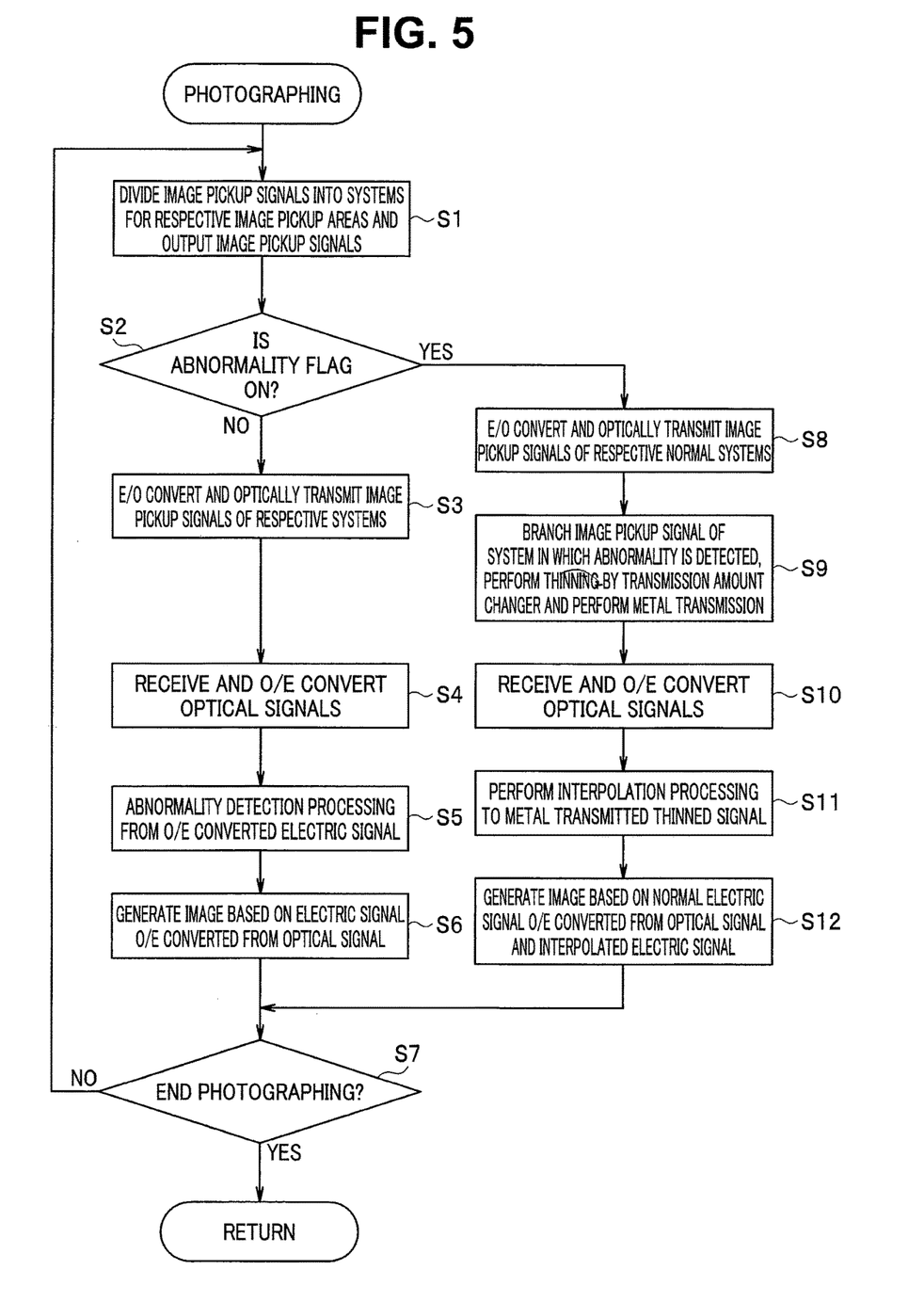
FIG. 5 is a flowchart illustrating an operation of the endoscope system in the embodiment 1.

Next, FIG. 5 is a flowchart illustrating an operation of the endoscope system 1.

A power source of the endoscope system 1 is turned on to start main processing not shown in the figure, and when photographing start is instructed in the main processing, photographing processing illustrated in FIG. 5 is started.

Then, the light receiving portion 12 picks up the image by the control of the control circuit 13, and the image pickup signals of two systems for which the light receiving portion 12 is divided into the image pickup area A1 and the image pickup area A2 as illustrated in FIG. 2 for example are outputted (step S1).

Subsequently, the abnormality detection portion 34 determines whether or not the abnormality flag is on (step S2).

Here, when it is determined that the abnormality flag is off, the abnormality detection portion 34 performs the control such that the switches 17a and 17b of the branching portion 17 are connected to the side of the E/O converters 18a and 18b. Thus, the image pickup signals of the respective systems are E/O converted and turned to the optical signals, and are transmitted through the optical fibers 21a and 21b to the signal processor 30 (step S3).

The optical signals transmitted through the optical fibers 21a and 21b are respective O/E converted by the O/E converters 33a and 33b and turned to the electric signals (step S4).

The abnormality detection portion 34 performs abnormality detection processing as described above, based on the electric signals O/E converted by the O/E converters 33a and 33b, and turns on the abnormality flag in the case that the abnormality is detected (step S5).

Further, the image processing portion 35 performs the image processing as described above and generates the video signal, based on the electric signals O/E converted by the O/E converters 33a and 33b (step S6). The video signal generated here is displayed at the display portion 40.

Thereafter, whether or not to end photographing is determined (step S7), and when it is determined that photographing is not to be ended, the operation returns to the processing of step S1 described above.

On the other hand, when it is determined that the abnormality flag is on in step S2, the abnormality detection portion 34 performs the control so as to switch the switch of the system relating to the optical fiber 21b or 21a in which the abnormality has occurred, which is the switch 17b or 17a of the branching portion 17, to the side of the transmission amount changer 19. However, the switch of the system with no abnormality is kept connected to the side of the optical fiber 21a or 21b.

Thus, the image pickup signal of a normal system is E/O converted by the E/O converter 18a or 18b and turned to the optical signal, and is transmitted through the optical fiber 21a or 21b to the signal processor 30 (step S8).

In addition, the image pickup signal of the system with the abnormality detected in the optical fiber is transmitted through the branching portion 17 to the transmission amount changer 19, decimated for example, and transmitted through the metal wire 22b to the image processing portion 35 (step S9).

The optical signal transmitted through the normal optical fiber 21a or 21b is O/E converted by the O/E converter 33a or 33b and turned to the electric signal (step S10).

The decimated image pickup signal transmitted through the metal wire 22b is interpolated as described above when inputted to the image processing portion 35 (step S11).

Then, the image processing portion 35 configures the image of the entire screen by integrating the image pickup signal O/E converted from the optical signal and the interpolated image pickup signal, performs the image processing as described above, and generates the video signal (step S12). The video signal generated here is also displayed at the display portion 40, similarly to step S6.

When the processing of step S12 is performed, the operation advances to step S7 described above.

In this way, when it is determined that photographing is to be ended in step S7, the operation returns from the photographing processing to the main processing not shown in the figure.

Note that, in the processing illustrated in FIG. 5, since the abnormality flag for which detection is performed in step S5 is determined in step S2 returning from a loop of step S7, even in the case that the abnormality is detected in step S5, the video signal is generated using the image pickup signal of an area where the abnormality has occurred and the image pickup signal of a normal area transmitted through the optical fibers 21a and 21b, only for one frame. However, without being limited to the configuration, for example, a frame buffer may be provided, and the video signal with abnormality occurrence of one frame before may be redisplayed, or the video signal may be generated and displayed using the image pickup signal of the area where the abnormality has not occurred of one frame before and the image pickup signal of the normal area of a present frame.

In addition, in the processing illustrated in FIG. 5, when the abnormality of the optical fiber 21b or 21a is once detected, the image pickup signal of the system with the abnormality detected in the optical fiber is transmitted through the metal wire 22b and the processing of steps S8-S12 is performed thereafter. However, without being limited to the configuration, the processing of the abnormality detection portion 34 may be repeatedly performed at an appropriate time interval, and when it is determined that the optical fiber 21b or 21a in which the abnormality is once detected has returned to normal, the processing of step S8-S12 may be shifted again to the processing of steps S3-S6.

According to such an embodiment 1, since the CMOS image pickup device 11 outputs the digital signals of the plurality of systems, the digital signals are converted to the optical signals respectively by the E/O converters 18a and 18b, and the plurality of optical fibers 21a and 21b transmit the respective optical signals (that is, the plurality of optical signals are transmitted in parallel), a transmission speed can be increased.

Further, since the metal wire 22b configured to transmit at least one system of the digital signal outputted from the CMOS image pickup device 11 is provided, even in the case that the abnormality occurs in either one of the plurality of optical fibers 21a and 21b, the digital signal of the system with the abnormality that has occurred in the optical fiber is transmitted by the metal wire 22b, and the image can be configured.

Then, even in the case that the abnormality occurs in a portion (optical fiber 21b or 21a) of the optical fibers, while the digital signal of the system in which the abnormality has occurred is transmitted by the metal wire 22b, the optical fiber 21a or 21b without the abnormality transmits the optical signal so that the image for which the image quality of the entire image does not substantially decline can be configured and observed.

In addition, since the transmission amount changer 19 converts the digital signal of at least one system to a digital signal of the data amount suitable for the transmission by the metal wire 22b, the digital signal can be transmitted by the metal wire 22b without causing data omission due to a transmission error.

Further, since the abnormality detection portion 34 detects the abnormality of the respective optical fibers 21a and 21b based on the electric signals for which the optical signals transmitted by the plurality of optical fibers 21a and 21b are converted respectively in the O/E converters 33a and 33b, the need of the configuration of irradiating the optical fibers 21a and 21b with separate light for detection or the like is eliminated, and the abnormality can be detected by a simple configuration.

Then, since the transmission amount changer 19 outputs only the digital signal of the system with the abnormality detected in the optical fiber to the metal wire 22b, it is not needed to allocate the data amount to the other signals and the digital signal of the highest image quality within a range that can be transmitted by the metal wire 22b can be transmitted.

In addition, since the image processing portion 35 generates the video signal based on the electric signals of the plurality of systems outputted from the O/E converters 33a and 33b in the case that the abnormality is not detected by the abnormality detection portion 34, and generates the video signal by combining the electric signal of the system with no abnormality detected, which is outputted from the O/E converters 33a and 33b, and the digital signal transmitted by the metal wire 22b in the case that the abnormality is detected by the abnormality detection portion 34, the image of the high image quality can be observed at normal time, and the image configured by the area of the high image quality and the area of declined image quality, for which the image quality of the entire image does not substantially decline, can be observed even when the abnormality occurs.

Furthermore, since the system of the digital signal outputted from the CMOS image pickup device 11 is for each of the plurality of image pickup areas for which a light receiving area is divided, the image of the high image quality and the image of the declined image quality can be obtained for each area.

For example, in the configuration of the image pickup areas A1 and A2 as illustrated in FIG. 2, when it is assumed that the image pickup area A1 is the high image quality and the image pickup area A2 is the declined image quality, by adjusting a composition so as to put a subject part desired to be observed with the high image quality in the image pickup area A1, a user can observe a target subject part with the high image quality even when the abnormality occurs in either one of the optical fibers 21a and 21b.

In addition, for example, in the case of dividing the image pickup area into an even-numbered line and an odd-numbered line, even when one line becomes the high image quality and the other line becomes the declined image quality, the image quality of the entire image can be turned to the image quality in a middle of the high image quality and the declined image quality, substantial image quality decline of an entire visual field can be suppressed, and relatively excellent image quality can be maintained.

Further, by the transmission amount changer 19 reducing the data amount of the digital signal by performing the decimation processing and the image processing portion 35 performing the interpolation processing on the digital signal transmitted by the metal wire 22b, the video signal according to a resolution of the image transmitted as the optical signal by the normal optical fiber 21a or 21b can be generated.

Then, by the transmission amount changer 19 changing the decimation rate of the decimation processing (or the compression rate of the data compression processing) and the image processing portion 35 changing the interpolation processing (or the data expansion processing corresponding to the compression rate) according to the number of the optical fibers 21a and 21b in which the abnormality is detected, the image can be configured even in the case that the abnormality occurs in the plurality of systems.

In addition, since the branching portion 17 which is the branching device performs switching so as to connect all the digital signals of the plurality of systems only to the E/O converters 18a and 18b at normal time, and connect all the digital signals of the normal system only to the E/O converters 18a and 18b and connect all the digital signals of the abnormal system only to the metal wire 22b at abnormal time, the transmission of the signals not used in the configuration of the image (for example, the transmission of the optical signal by the optical fiber in which the abnormality has occurred, or redundant transmission by the metal wire 22b of the digital signal of the same system as the digital signal transmitted by the normal optical fiber) is not performed, unneeded processing is reduced, and power consumption can be reduced.

Furthermore, since the plurality of optical fibers 21a and 21b arranged in parallel are used as the optical transmitting members, shape change such as bending of the connection cable 20 becomes possible as long as the curvature is within an allowable range, and handling becomes easy.

Note that the respective portions described above may be configured as circuits. Then, an arbitrary circuit may be mounted as a single circuit or may be mounted as a combination of a plurality of circuits as long as the same function can be achieved. Further, the arbitrary circuit is not limited to the configuration as an exclusive circuit for achieving a target function, and may be configured to achieve the target function by making a general purpose circuit execute a processing program.

In addition, while the endoscope system is mainly described above, an operation method configured to operate the endoscope system as described above may be described, or a processing program for making a computer perform the processing similar to the processing of the endoscope system or a computer-readable non-transitory recording medium configured to record the processing program or the like may be described.

Further, the present invention is not limited to the above-described embodiment as it is, and components can be modified and embodied without departing from the scope in an implementation phase. In addition, by an appropriate combination of the plurality of components disclosed in the embodiment described above, various invention aspects can be formed. For example, some components may be deleted from all the components indicated in the embodiment. Further, the components over the different embodiments may be appropriately combined. In this way, it is needless to say that various modifications and applications are possible without changing a gist of the invention.

What is claimed is:

1. An endoscope system comprising:
an image pickup apparatus configured to pick up an image of a subject and output the image as digital signals of a plurality of systems;
an electrooptic converter configured to convert the digital signals of the plurality of systems outputted from the image pickup apparatus to optical signals respectively and output the optical signals;
a plurality of optical transmitting members configured to respectively transmit the optical signals of the plurality of systems outputted from the electrooptic converter;
a metal transmitting member configured to transmit a digital signal of at least one system among the digital signals of the plurality of systems outputted from the image pickup apparatus;
a transmission amount changer configured to convert the digital signal of at least one system which is a target to be transmitted by the metal transmitting member to a digital signal of a data amount suitable for transmission by the metal transmitting member, and output the digital signal to the metal transmitting member;
an optoelectric converter configured to convert the optical signals transmitted by the plurality of optical transmitting members to electric signals respectively and output the electric signals; and
an abnormality detector configured to detect abnormality of each of the plurality of optical transmitting members, based on the electric signals outputted from the optoelectric converter,
wherein the transmission amount changer is configured to convert only the digital signal of the system transmitted by one or more of the plurality of optical transmitting members in which the abnormality is detected by the abnormality detector to the digital signal of the data amount suitable for the transmission by the metal transmitting member, and output the digital signal to the metal transmitting member.

2. The endoscope system according to claim 1, further comprising a video signal generator configured to generate a video signal based on the electric signals of the plurality of systems outputted from the optoelectric converter in a case that the abnormality is not detected by the abnormality detector, and generate a video signal by combining one or more of the electric signals of the one or more systems with no abnormality detected, which is outputted from the optoelectric converter, and the digital signal transmitted by the metal transmitting member in a case that the abnormality is detected by the abnormality detector.

3. The endoscope system according to claim 2,
wherein the image pickup apparatus is configured to divide a light receiving area to pick up the image of the subject into a plurality of image pickup areas, define the digital signal obtained from one of the image pickup areas as one system and output the digital signals of the plurality of systems.

4. The endoscope system according to claim 2,
wherein the transmission amount changer is configured to convert the data amount by performing decimation processing on the digital signal and reducing the data amount of the digital signal, and
wherein in the case that the abnormality is detected by the abnormality detector, the video signal generator is configured to perform interpolation processing on the digital signal transmitted by the metal transmitting member, and then generate the video signal by combining the digital signal with the electric signal of the system with no abnormality detected, which is outputted from the optoelectric converter.

5. The endoscope system according to claim 4,
wherein the transmission amount changer is configured to change a decimation rate of the decimation processing according to a number of the optical transmitting members in which the abnormality is detected by the abnormality detector, and
wherein the video signal generator changes the interpolation processing according to the decimation rate.

6. The endoscope system according to claim 2,
wherein the transmission amount changer is configured to convert the data amount by performing data compression processing on the digital signal and reducing the data amount of the digital signal, and
wherein in the case that the abnormality is detected by the abnormality detector, the video signal generator is configured to perform data expansion processing on the digital signal transmitted by the metal transmitting member, and then generate the video signal by combining the digital signal with the electric signal of the system with no abnormality detected, which is outputted from the optoelectric converter.

7. The endoscope system according to claim 6,
wherein the transmission amount changer is configured to change a compression rate of the data compression processing according to a number of the optical transmitting members in which the abnormality is detected by the abnormality detector, and
wherein the video signal generator is configured to change the data expansion processing according to the compression rate.

8. The endoscope system according to claim 1, further comprising a branching device configured to perform switching so as to connect all the digital signals of the plurality of systems outputted from the image pickup apparatus only to the electrooptic converter in the case that the abnormality is not detected by the abnormality detector, and connect all the digital signals of the system transmitted by one or more the optical transmitting members in which the abnormality is not detected among the digital signals of the plurality of systems outputted from the image pickup apparatus only to the electrooptic converter and connect all the digital signals of the system transmitted by one or more the optical transmitting members in which the abnormality is detected only to the metal transmitting member in the case that the abnormality is detected by the abnormality detector.

9. The endoscope system according to claim 1,
wherein the plurality of optical transmitting members comprises a plurality of optical fibers arranged in parallel.

10. An operation method of an endoscope system, wherein the operation method comprises:
an image pickup apparatus picking up an image of a subject and outputting the image as digital signals of a plurality of systems,
an electrooptic converter converting the digital signals of the plurality of systems outputted from the image pickup apparatus to optical signals respectively and outputting the optical signals;
a plurality of optical transmitting members respectively transmitting the optical signals of the plurality of systems outputted from the electrooptic converter;
a metal transmitting member transmitting a digital signal of at least one system among the digital signals of the plurality of systems outputted from the image pickup apparatus;
a transmission amount changer converting the digital signal of at least one system which is a target to be transmitted by the metal transmitting member to a digital signal of a data amount suitable for transmission by the metal transmitting member, and outputting the digital signal to the metal transmitting member;
an optoelectric converter converting the optical signals transmitted by the plurality of optical transmitting members to electric signals respectively and outputting the electric signals;
an abnormality detector detecting abnormality of each of the plurality of optical transmitting members, based on the electric signals outputted from the optoelectric converter; and
wherein the transmission amount changer converts only the digital signal of the system transmitted by one or more of the plurality of optical transmitting members in which the abnormality is detected by the abnormality detector to the digital signal of the data amount suitable for the transmission by the metal transmitting member, and outputs the digital signal to the metal transmitting member.

* * * * *